United States Patent
Bucciaglia et al.

(10) Patent No.: US 8,246,618 B2
(45) Date of Patent: Aug. 21, 2012

(54) ELECTROSURGICAL JAWS WITH OFFSET KNIFE

(75) Inventors: Joseph D. Bucciaglia, Louisville, CO (US); Edward M. Chojin, Boulder, CO (US); Glenn A. Horner, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 511 days.

(21) Appl. No.: 12/499,553

(22) Filed: Jul. 8, 2009

(65) Prior Publication Data

US 2011/0009864 A1    Jan. 13, 2011

(51) Int. Cl.
*A61B 18/14* (2006.01)
(52) U.S. Cl. .......................................... 606/51; 606/46
(58) Field of Classification Search .................. 606/45, 606/46, 50–52
See application file for complete search history.

(56) References Cited

U.S. PATENT DOCUMENTS

| | | | |
|---|---|---|---|
| 5,389,098 A * | 2/1995 | Tsuruta et al. .................. 606/41 |
| 5,458,598 A * | 10/1995 | Feinberg et al. ................ 606/52 |
| 5,735,849 A * | 4/1998 | Baden et al. .................... 606/51 |
| 5,755,717 A | 5/1998 | Yates et al. |
| 5,797,941 A | 8/1998 | Schulze et al. |
| 5,797,958 A | 8/1998 | Yoon |
| 5,984,939 A | 11/1999 | Yoon |
| 6,500,176 B1 * | 12/2002 | Truckai et al. .................. 606/51 |
| 7,011,657 B2 | 3/2006 | Truckai et al. |
| 7,442,194 B2 | 10/2008 | Dumbauld et al. |
| 7,473,253 B2 | 1/2009 | Dycus et al. |
| 7,481,810 B2 | 1/2009 | Dumbauld et al. |
| 7,887,536 B2 | 2/2011 | Johnson |
| 8,016,827 B2 | 9/2011 | Chojin |
| 8,114,122 B2 | 2/2012 | Nau, Jr. |
| 2003/0018331 A1 * | 1/2003 | Dycus et al. .................... 606/48 |
| 2005/0154387 A1 | 7/2005 | Moses |
| 2007/0078456 A1 | 4/2007 | Dumbauld |
| 2009/0250613 A1 | 10/2009 | Myrick |
| 2010/0016857 A1 | 1/2010 | McKenna |
| 2010/0023009 A1 | 1/2010 | Moses |

(Continued)

FOREIGN PATENT DOCUMENTS

DE    2415263    10/1975

(Continued)

OTHER PUBLICATIONS

International Search Report EP10168705 dated Apr. 10, 2010.

(Continued)

*Primary Examiner* — Michael Peffley

(57) ABSTRACT

An endoscopic forceps includes a housing having a shaft attached thereto with a longitudinal axis defined therethrough and an end effector assembly disposed at a distal end thereof. The end effector assembly includes first and second jaw members disposed in opposing relation relative to one another and moveable from a first, open position to a second, closed position for grasping tissue therebetween. Each of the jaw members includes a proximal flange adapted to communicate with a drive assembly for moving the jaw members between the first and second positions. One or both of the of the jaw members has a curved knife channel defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough.

18 Claims, 11 Drawing Sheets

U.S. PATENT DOCUMENTS

| | | |
|---|---|---|
| 2010/0036375 A1 | 2/2010 | Regadas |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0087818 A1 | 4/2010 | Cunningham |
| 2010/0094287 A1 | 4/2010 | Cunningham |
| 2010/0100122 A1 | 4/2010 | Hinton |
| 2010/0145334 A1 | 6/2010 | Olson |
| 2010/0179545 A1 | 7/2010 | Twomey |
| 2010/0179546 A1 | 7/2010 | Cunningham |
| 2010/0179547 A1 | 7/2010 | Cunningham |
| 2010/0249769 A1 | 9/2010 | Nau, Jr. |
| 2010/0249776 A1 | 9/2010 | Kerr |
| 2010/0256635 A1 | 10/2010 | McKenna |
| 2010/0280511 A1 | 11/2010 | Rachlin |
| 2011/0015632 A1 | 1/2011 | Artale |
| 2011/0034918 A1 | 2/2011 | Reschke |
| 2011/0046623 A1 | 2/2011 | Reschke |
| 2011/0054467 A1 | 3/2011 | Mueller |
| 2011/0054468 A1 | 3/2011 | Dycus |
| 2011/0054469 A1 | 3/2011 | Kappus |
| 2011/0054471 A1 | 3/2011 | Gerhardt |
| 2011/0054472 A1 | 3/2011 | Romero |
| 2011/0060333 A1 | 3/2011 | Mueller |
| 2011/0060334 A1 | 3/2011 | Brandt |
| 2011/0060335 A1 | 3/2011 | Harper |
| 2011/0060356 A1 | 3/2011 | Reschke |
| 2011/0071522 A1 | 3/2011 | Dumbauld |
| 2011/0071523 A1 | 3/2011 | Dickhans |
| 2011/0072638 A1 | 3/2011 | Brandt |
| 2011/0073246 A1 | 3/2011 | Brandt |
| 2011/0077648 A1 | 3/2011 | Lee |
| 2011/0077649 A1 | 3/2011 | Kingsley |
| 2011/0082457 A1 | 4/2011 | Kerr |
| 2011/0082494 A1 | 4/2011 | Kerr |
| 2011/0087221 A1 | 4/2011 | Siebrecht |
| 2011/0098689 A1 | 4/2011 | Nau, Jr. |
| 2011/0184405 A1* | 7/2011 | Mueller .................. 606/41 |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 1159926 | 12/2001 |
| EP | 1649821 | 4/2006 |
| EP | 1810625 | 7/2007 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Michael Choti, "Abdominoperineal Resection with the LigaSure Vessel Sealing System and LigaSure Atlas 20 cm Open Instrument" ; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

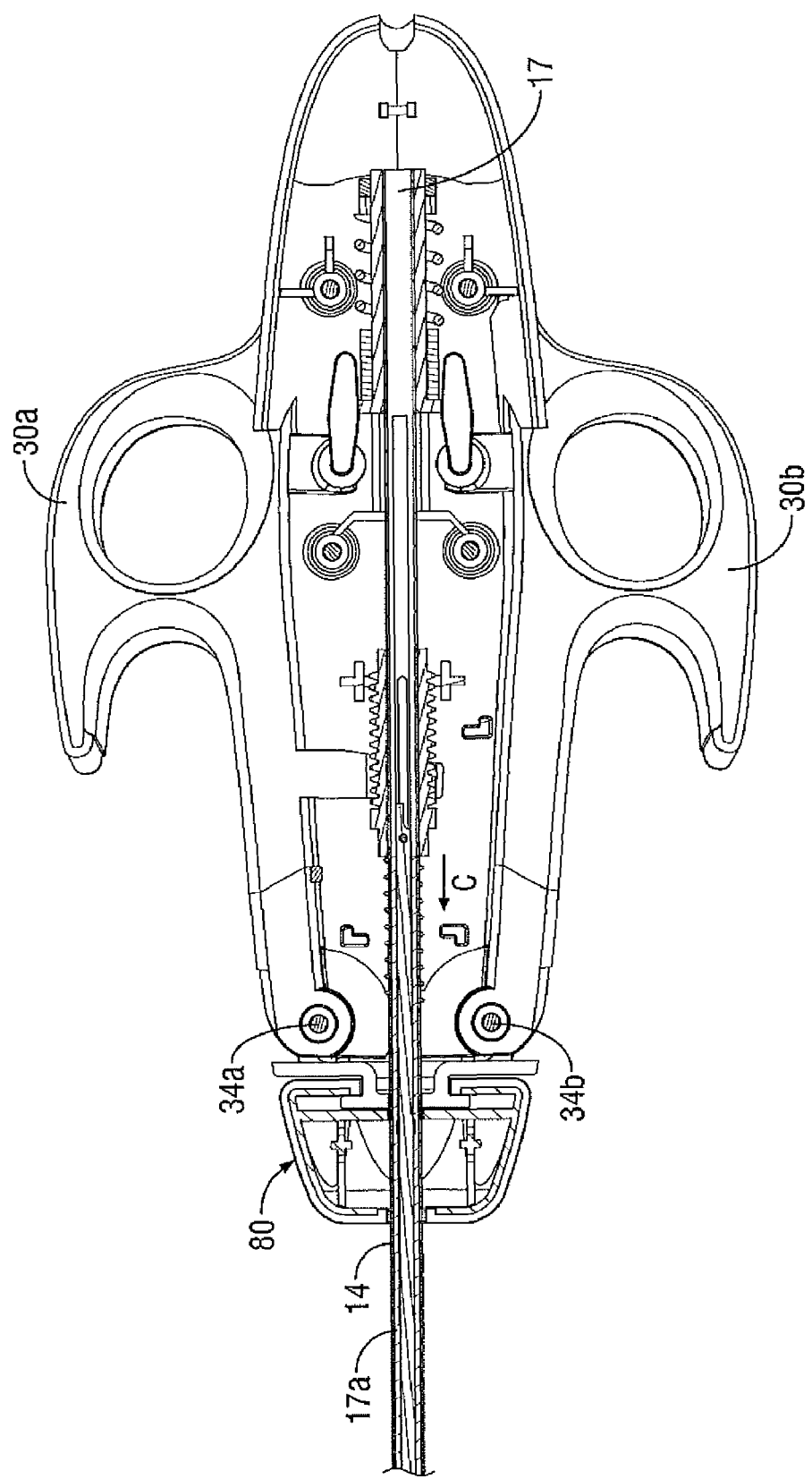

ELECTROSURGICAL JAWS WITH OFFSET KNIFE

BACKGROUND

The present disclosure relates to an electrosurgical jaws and, more particularly, to an elongated endoscopic electrosurgical forceps with an offset knife for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

Typically, after a vessel or tissue is sealed, the surgeon advances a knife to sever the sealed tissue disposed between the opposing jaw members. In some instances, the knife blade is difficult to advance through the knife channel defined between jaw members or is subject to wear and tear over repeated use due to the relative position of the knife blade through the knife channel (contacting the sides of the knife channel).

SUMMARY

The present disclosure relates to an endoscopic forceps that includes a housing having a shaft attached thereto with a longitudinal axis defined therethrough. An end effector assembly is disposed at a distal end thereof and includes first and second jaw members disposed in opposing relation relative to one another and moveable from a first, open position to a second, closed position for grasping tissue therebetween. Each of the jaw members includes a proximal flange adapted to communicate with a drive assembly for moving the jaw members between the first and second positions. One or both of the of the jaw members has a curved knife channel (or a portion, e.g., distal portion, of the knife channel is curved) defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough. One or more handles may be included that operably couple to the drive assembly for moving the jaw members between the first and second positions.

In one embodiment, the endoscopic forceps is an electrosurgical instrument and at least one of the jaw members is adapted to connect to an electrosurgical energy source to communicate energy to tissue disposed between the jaw members.

In another embodiment, the proximal flanges of the end effector and the knife guide include elongated slots defined therethrough that cooperate with a drive pin operably connected to the drive assembly to move the jaw members from the first to second positions. The elongated slots of the proximal flanges may be cam slots that operably engage the drive pin and the elongated slot of the knife guide may be a pass-through or non-engaging slot.

In yet another embodiment, the offset knife channel and the disposition of the knife guide relative to the longitudinal axis facilitate substantially straight extension of the knife through the knife channel along a substantial length of the knife channel. This configuration helps prevent binding of the knife during translation through the knife channel. The proximal end of the knife channel may be offset a distance "X" relative to the longitudinal axis "A" defined through the forceps, wherein "X" is in the range of about 0.010 inches to about 0.040 inches. The knife channel may be defined within both the first and second jaw members and the knife guide is configured to preload the jaw members during assembly for ensuring proper alignment of the knife channels to facilitate translation of the knife therethrough.

In still yet another embodiment, the knife guide includes one or more channels defined therein that are configured to guide a corresponding number of electrical leads to the jaw member(s) for supplying electrosurgical energy thereto.

The present disclosure also relates to an endoscopic forceps that includes a housing having a shaft attached thereto with a longitudinal axis defined therethrough and an end effector assembly disposed at a distal end thereof. The end effector assembly includes first and second jaw members disposed in opposing relation relative to one another and moveable from a first, open configuration to a second, closed configuration for grasping tissue therebetween. Each of the jaw members includes a proximal flange adapted to communicate with a drive assembly for moving the jaw members between the first and second positions. One or both of the of the jaw members has a knife channel defined therein having a proximal end that is offset from the longitudinal axis defined through the shaft. A knife guide is assembled to an outer surface of one of the proximal flanges of the jaw members on the same side as the proximal end of the knife channel and defines a knife path therein configured to guide a knife into the knife channel for translation therethrough. The knife guide includes a blade stop at a distal end thereof that is positionable from a first position that interferes with or obstructs the knife path to prevent distal translation of the knife when the jaw members are disposed in an first, open configuration to a second position that allows distal translation of the knife when the jaw members are disposed in the second, closed configuration. The blade stop may be pivotably engaged to the knife guide and biased to obstruct the knife path when the jaw members are disposed in the first, open configuration.

The forceps may include one or more handles that operably couple to a drive assembly for moving the jaw members between the first and second configurations. Moreover, the forceps may be an electrosurgical forceps wherein one or both of the jaw members are adapted to connect to an electrosurgical energy source to communicate energy to tissue disposed between the jaw members.

The proximal flanges of the end effector and the knife guide may include elongated slots defined therethrough that cooperate with a drive pin operably connected to the drive assembly to move the jaw members from the first to second configurations. The elongated slots of the proximal flanges may be cam slots that operably engage the drive pin and the elongated slot of the knife guide may be a pass-through or non-engaging slot.

In another embodiment, the offset knife channel and the disposition of the knife guide relative to the longitudinal axis may be configured to facilitate substantially straight extension of the knife through the knife channel along a substantial length of the knife channel. The proximal end of the knife channel may be offset a distance "X" relative to the longitudinal axis "A" defined through the forceps, wherein "X" is in the range of about 0.010 inches to about 0.040 inches.

In yet another embodiment, the knife guide includes one or more channels defined therein that are configured to guide a corresponding number of electrical leads to the jaw member for supplying electrosurgical energy thereto.

BRIEF DESCRIPTION OF THE DRAWINGS

Various embodiments of the subject instrument are described herein with reference to the drawings wherein:

FIG. 3A is an enlarged, top view showing the knife actuator after actuation;

DETAILED DESCRIPTION

Figure 1A:
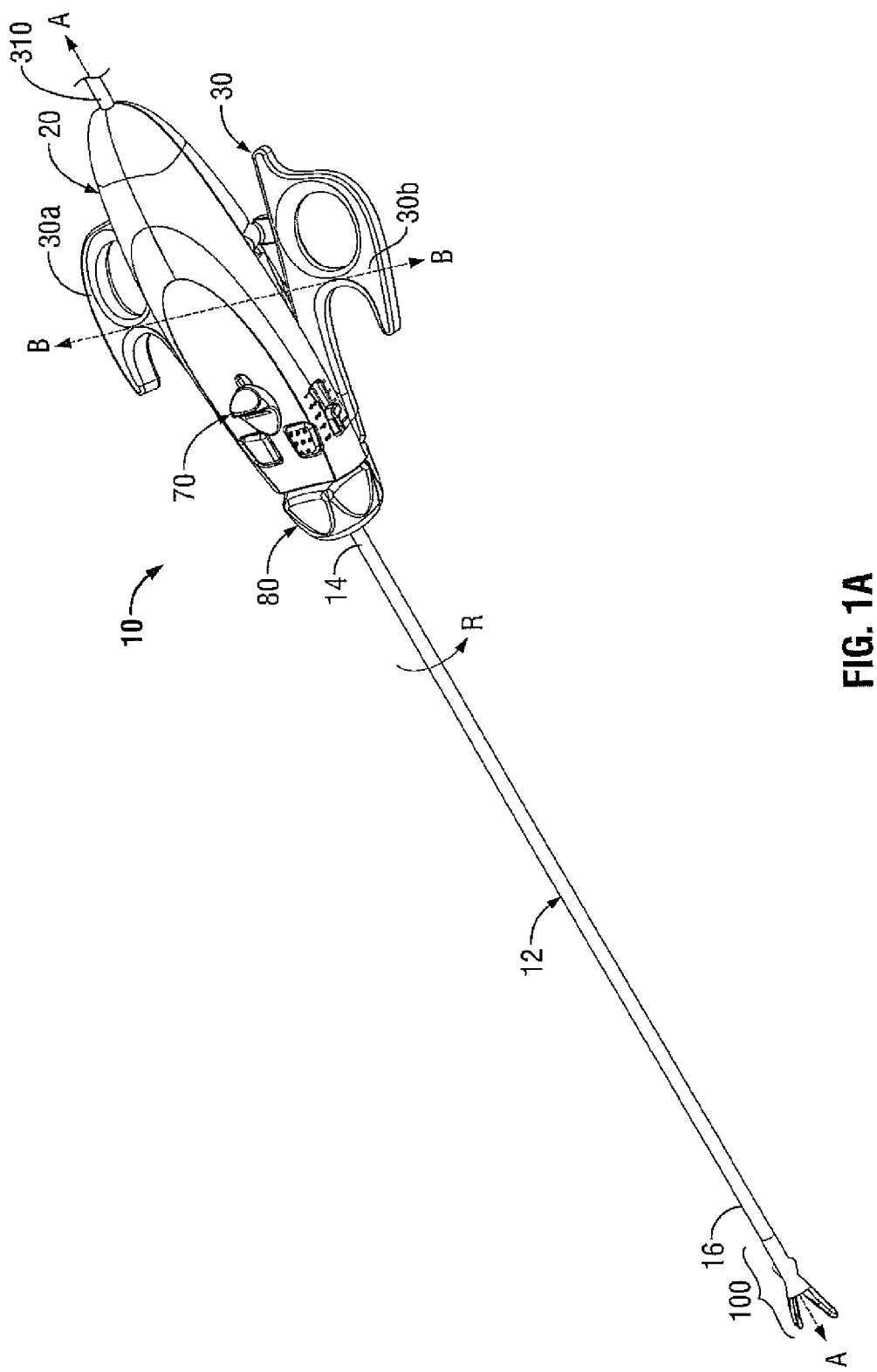
FIG. 1A is a top, perspective view of an endoscopic forceps shown in an open configuration and including a housing, a handle assembly, a shaft and an end effector assembly according to the present disclosure.
Figure 1B:
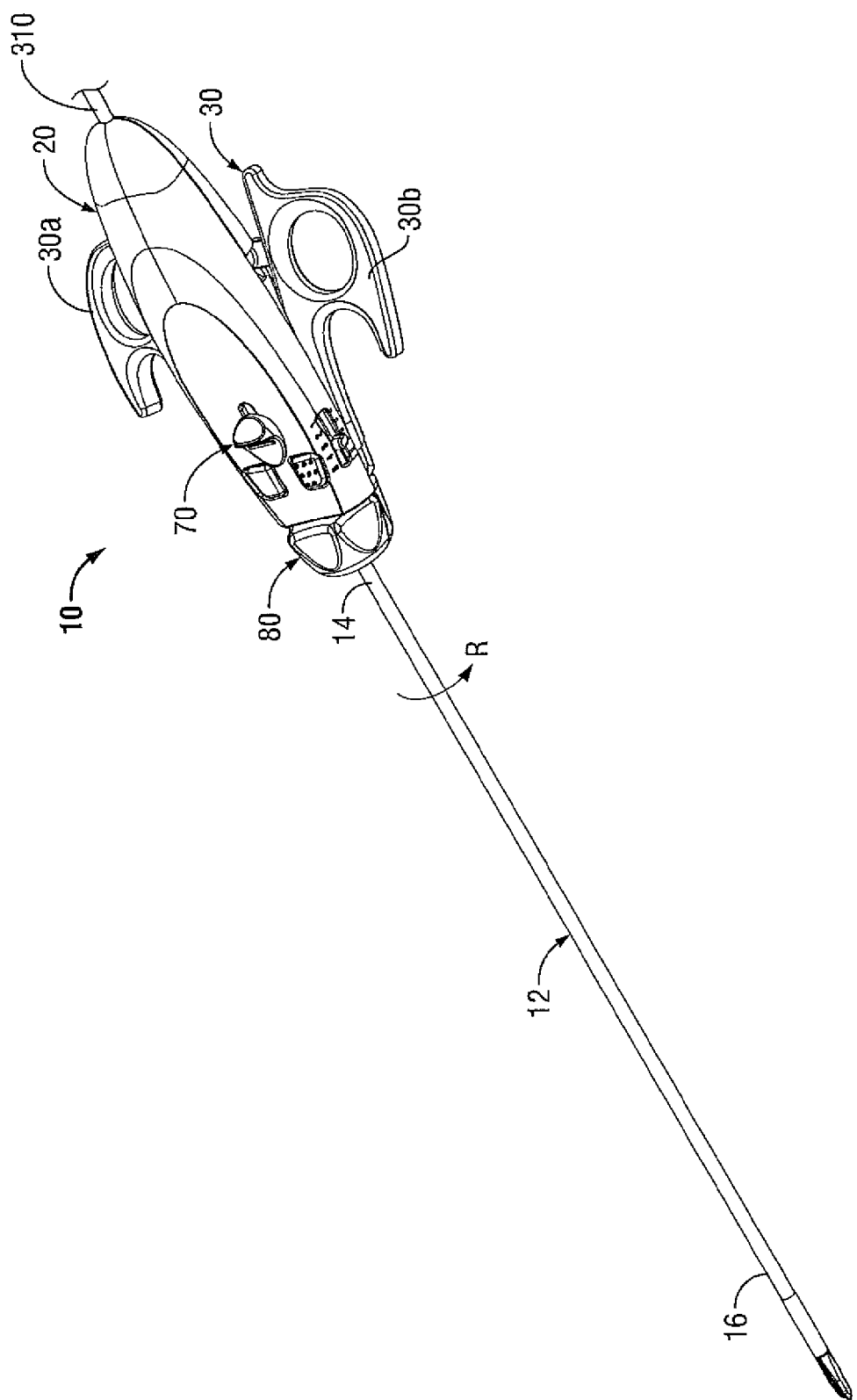
FIG. 1B is a top, perspective view of the endoscopic forceps of FIG. 1A showing the end effector assembly in a closed configuration according to the present disclosure.

Turning now to FIGS. 1A and 1B, one embodiment of an electrosurgical forceps 10 is shown for use with various surgical procedures and generally includes a housing 20, a handle assembly 30, a rotating assembly 80, a knife trigger assembly 70 and an end effector assembly 100 which mutually cooperate to grasp, seal and divide tubular vessels and vascular tissue. Although the majority of the figure drawings depict a forceps 10 for use in connection with endoscopic or laparoscopic surgical procedures, the present disclosure may be used for more traditional open surgical procedures. For the purposes herein, the forceps 10 is described In terms of an endoscopic or laparoscopic instrument; however, it is contemplated that an open version of the forceps may also include the same or similar operating components and features as described below.

Forceps 10 includes a shaft 12 that has a distal end 16 dimensioned to mechanically engage the end effector assembly 100 and a proximal end 14 that mechanically engages the housing 20. Details of how the shaft 12 connects to the end effector assembly 100 are described in more detail below. The proximal end 14 of shaft 12 is received within the housing 20 and the connections relating thereto are also described in detail below. In the drawings and in the descriptions that follow, the term "proximal", as is traditional, will refer to the end of the forceps 10 that is closer to the user, while the term "distal" will refer to the end that is further from the user.

Forceps 10 also includes an electrosurgical cable 310 that may connect the forceps 10 to a source of electrosurgical energy, e.g., a generator. Generators such as those sold by Covidien, located in Boulder, Colo. may be used as a source of both bipolar electrosurgical energy for sealing vessel and vascular tissues as well as monopolar electrosurgical energy which is typically employed to coagulate or cauterize tissue. It is envisioned that the generator may include various safety and performance features including isolated output, impedance control and/or independent activation of accessories.

Handle assembly 30 includes two movable handles 30a and 30b disposed on opposite sides of housing 20. Handles 30a and 30b are movable relative to one another to actuate the end effector assembly 100 as explained in more detail below with respect to the operation of the forceps 10.

Rotating assembly 80 is mechanically coupled to housing 20 and is rotatable approximately 90 degrees in either direction about a longitudinal axis "A." Rotating assembly 80, when rotated, rotates shaft 12, which, in turn, rotates end effector assembly 100. Such a configuration allows end effector assembly 100 to be rotated approximately 90 degrees in either direction with respect to housing 20.

Figure 6:
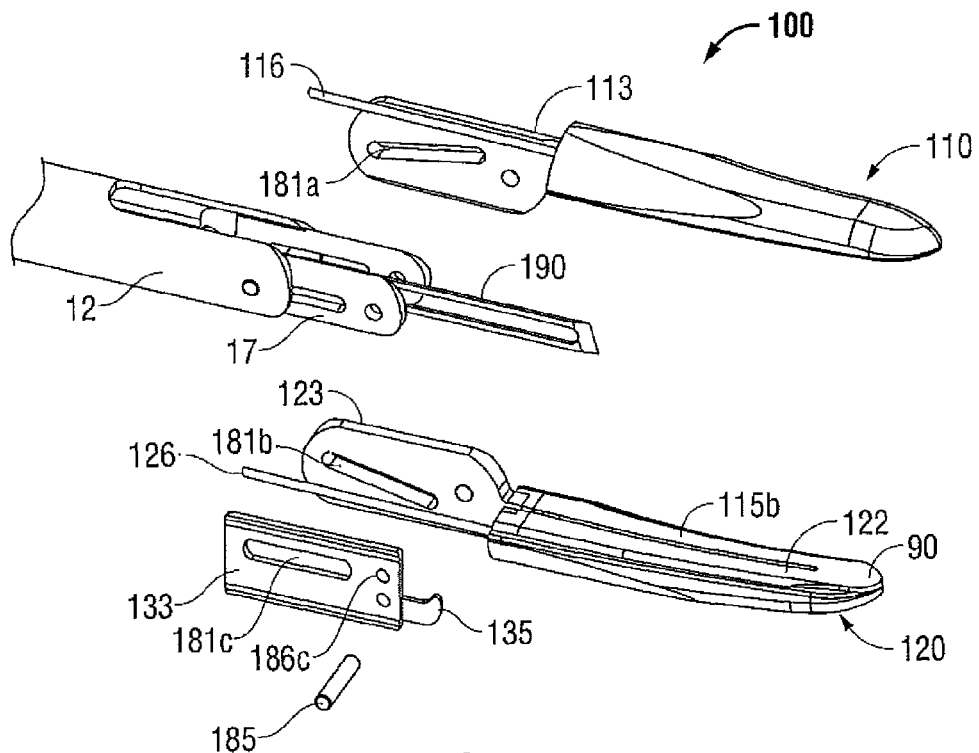
FIG. 6 is a partially exploded, perspective view of the end effector assembly.

As mentioned above, end effector assembly 100 is attached at the distal end 16 of shaft 12 and includes a pair of opposing jaw members 110 and 120 (see FIG. 6). Handles 30a and 30b of handle assembly 30 ultimately connect to drive assembly 60 (see FIG. 2A) which, together, mechanically cooperate to impart movement of the jaw members 110 and 120 from a first, open position wherein the jaw members 110 and 120 are disposed in spaced relation relative to one another, to a second, clamping or closed position wherein the jaw members 110 and 120 cooperate to grasp tissue therebetween.

Turning now to the more detailed features of the present disclosure as described with respect to FIGS. 1A-8C, handles 30a and 30b each include an aperture 33a and 33b, respectively, defined therein which enables a user to grasp and move each respective handle 30a and 30b relative to one another. Handles 30a and 30b also include ergonomically-enhanced gripping elements 39a and 39b, respectively, disposed along an outer edge thereof which are designed to facilitate gripping of the handles 30a and 30b during activation. It is envisioned that gripping elements 39a and 39b may include one or more protuberances, scallops and/or ribs to enhance gripping.

As best illustrated in FIG. 1A, handles 30a and 30b are configured to extend outwardly on opposite sides from a transverse axis "B" defined through housing 20 which is perpendicular to longitudinal axis "A". Handles 30a and 30b are movable relative to one another in a direction parallel to axis "B" to open and close the jaw members 110 and 120 as needed during surgery. Details relating to the inner-working components of forceps 10 are disclosed in commonly-owned U.S. patent application Ser. No. 11/540,335. This forceps style is commonly referred to as an "in-line" or hemostat style forceps. In-line hemostats or forceps are more commonly manufactured for open surgical procedures and typically include a pair of shafts having integrally coupled handles which are movable relative to one another to open and close the jaw members disposed at the distal end thereof.

Figure 2A:
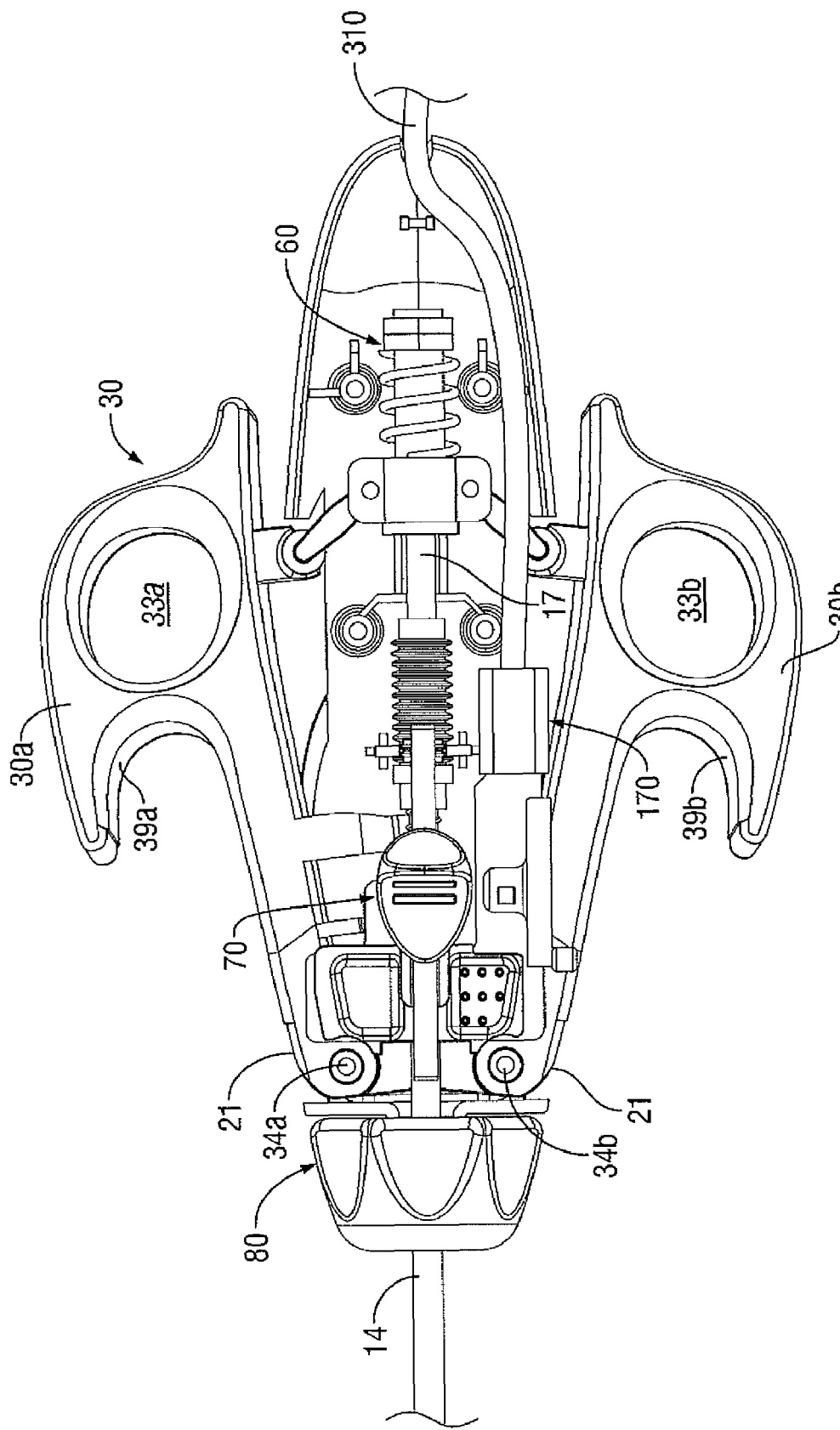
FIG. 2A is an enlarged, top view of the forceps of FIG. 1A showing the disposition of the internal components when the forceps is in an open configuration.
Figure 2B:
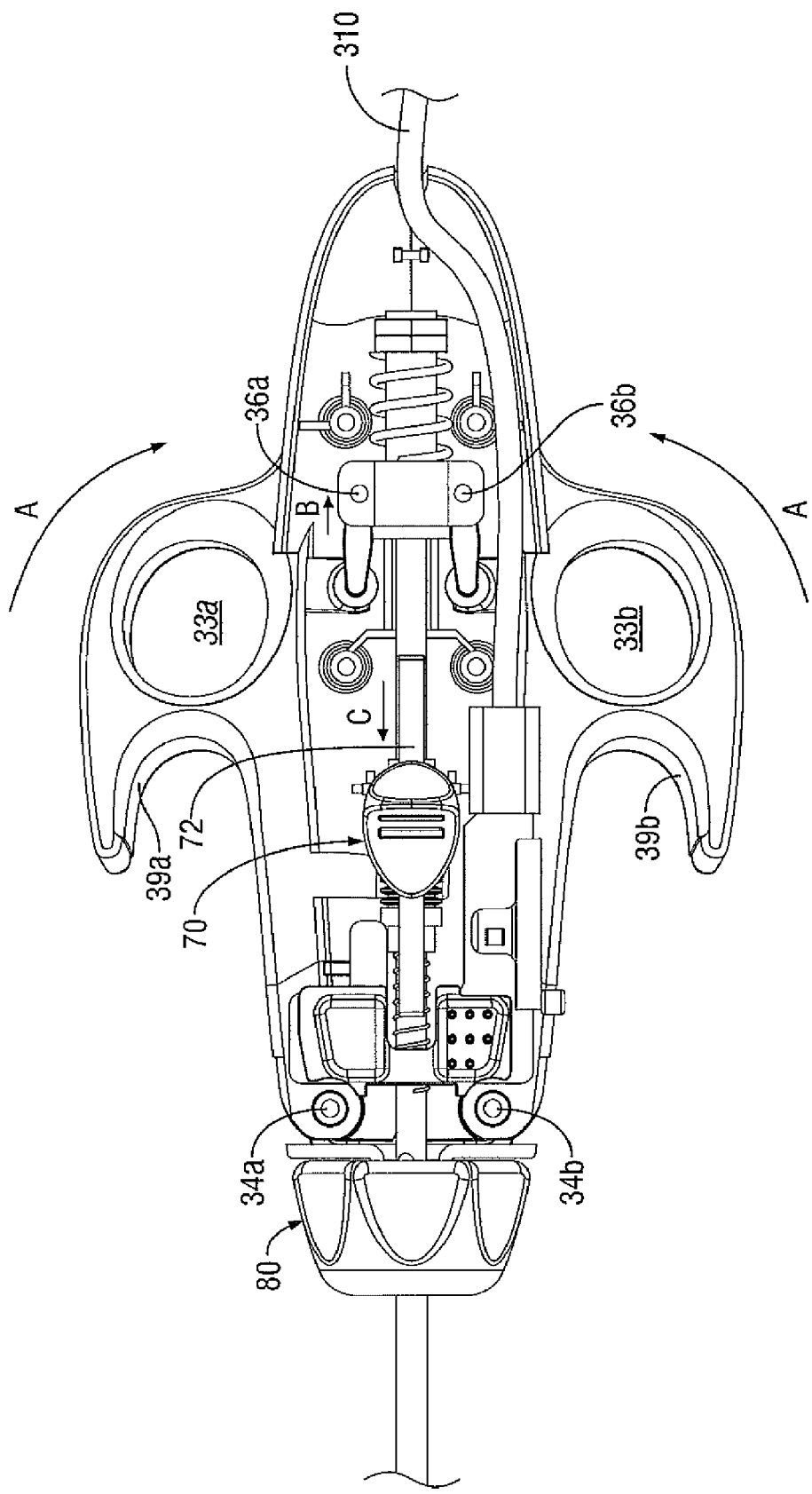
FIG. 2B is an enlarged, top view of the forceps of FIG. 1B showing the disposition of the internal components when the forceps is in a closed configuration.
Figure 3B:
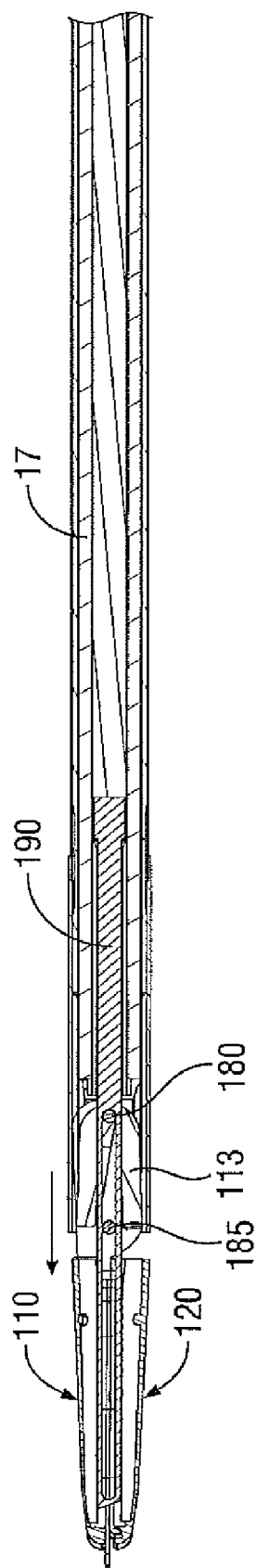
FIG. 3B is a greatly-enlarged, side cross sectional view of the end effector assembly showing the position of the knife after actuation.

As best seen in FIGS. 2A and 2B, the distal end of each handle 30a and 30b is selectively moveable about pivot pins 34a and 34b attached to a distal end 21 of the housing 20 to actuate the jaw members 110 and 120. Movement of the handles 30a and 30b away from one another (and the housing 20) unlocks and opens the handles 30a and 30b and, in turn, the jaw members 110 and 120 for subsequent grasping or re-grasping of tissue. In one embodiment, the handles 30a and 30b may be biased in an open configuration to facilitate handling and manipulation of the jaws within an operative field. Various spring-like mechanisms are contemplated which may be utilized to accomplish this purpose.

Movable handles 30a and 30b are designed to provide a distinct lever-like mechanical advantage over conventional handle assemblies. The enhanced mechanical advantage for actuating the jaw members 110 and 120 is gained by virtue of the unique position and combination of several inter-cooperating elements which reduce the overall user forces necessary to obtain and maintain the jaw members 110 and 120 under ideal operating pressures of about 3 kg/cm$^2$ to about 16 kg/cm$^2$. Details relating to the working components the handle assembly and drive assembly are disclosed in above-mentioned U.S. patent application Ser. No. 11/540,335. In other words, it is envisioned that the combination of these elements and their positions relative to one another enables the user to gain lever-like mechanical advantage to actuate the jaw members 110 and 120 enabling the user to close the jaw members 110 and 120 with lesser force while still generating the required forces necessary to effect a proper and effective tissue seal.

As shown best in FIGS. 4A, 4B, 5 and 6, the end effector assembly 100 is designed as a bilateral assembly, i.e., both jaw members 110 and 120 pivot relative to one another about a pivot pin 185 disposed therethrough. A unilateral end effector assembly is also envisioned. End effector assembly 100 further includes a knife guide 133 that houses the knife blade 190 for translation therethrough. Knife guide 133 is assembled with flanges 113 and 123 to allow pivotable movement of the flanges 113 and 123 about a pivot pin 185 disposed between the jaw members 110 and 120 upon translation of a drive pin 180 as explained in more detail below.

More particularly, jaw members 110 and 120 include proximal flanges 113 and 123, respectively, which each include an elongated angled slot 181a and 181b, respectively, defined therethrough. Drive pin 180 mounts jaw members 110 and 120 and knife guide 133 to the end of a rotating shaft 18 and within a cavity 17' defined at the distal ends 17a and 17b of drive actuator or sleeve 17 (See FIG. 5). Knife guide 133 includes an elongated slot 181c defined therethrough, configured for accepting the drive pin 180 and for allowing translation of the drive pin 180 within slots 181a-181c, which pivots the jaw members 110 and 120 relative to one another for grasping tissue. Knife guide 133 may also provide a unique safety feature for the forceps 10 as described in more detail below.

Upon actuation of the drive assembly 60, the drive sleeve 17 reciprocates which, in turn, causes the drive pin 180 to ride within slots 181a and 181b to open and close the jaw members 110 and 120 as desired and similarly causes the drive pin 180 to ride within slot 181c of knife guide 133. The jaw members 110 and 120, in turn, pivot about pivot pin 185 disposed through respective pivot holes 186a and 186b defined within flanges 113 and 123, the jaw members 110 and 120 and hole 186c disposed within knife guide 133. Upon actuation, knife guide 133 remains oriented in alignment with the shaft 12 as the jaws move about pivot pin 185 (See FIG. 6). As can be appreciated, squeezing handles 30a and 30b toward the housing 20 pulls drive sleeve 17 and drive pin 180 proximally to close the jaw members 110 and 120 about tissue grasped therebetween and pushing the sleeve 17 distally opens the jaw members 110 and 120 for grasping purposes.

Figure 7:
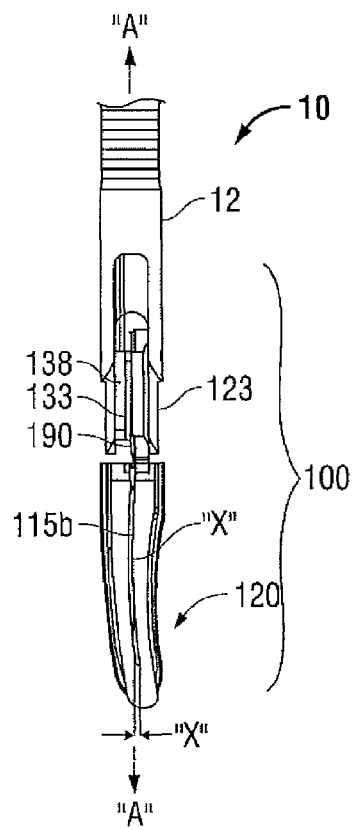
FIG. 7 is a top view of the end effector assembly with the upper jaw member removed.

Flanges 113 and 123 of jaw members 110 and 120, respectively, are positioned in an abutting relationship with one another and knife guide 133 is positioned adjacent to flanges 113 and 123. Flanges 113, 123 and knife guide 133 are assembled and engaged via pivot pin 185 disposed through apertures 186a, 186b, and 186c, respectively. Further, flanges 113, 123 are pivotable about one another via drive pin 180 disposed through slots 181a and 181b and of flanges 113, 123, respectively. A knife path 138 may be defined between flange 113 and knife guide 133, as shown in FIGS. 6 and 7. The knife path 138 longitudinally aligns with knife channels 115a and 115b defined within jaw members 110 and 120, such that knife blade 190 travels in a substantially straight path through knife path 138 and, further, through knife channels 115a and 115b.

Alternatively, the orientation of flanges 113 and 123 may be reversed, with knife path 138 being defined between flange 123 and blade guide 133. In contrast to prior known designs, the abutting relationship between flanges 113 and 123 (in either orientation) strengthens the jaw flanges 113 and 123 since a blade path or blade channel does not need to be defined therebetween but, rather, is defined on an exterior side of one of the flanges 113 and 123. Thus, the knife 190 travels between the blade guide 133 and the flanges 113 and 123 and not between flanges. By manufacturing the knife path 138 on either side of the flanges 113 and 123, jaw splay may also be more easily controlled and tighter tolerances may be employed during the manufacturing process, thereby allowing tighter tolerances on certain features of the jaw member 110 and 120 resulting in better overall performance.

For example, the knife channels 115a and 115b defined within the jaw members 110 and 120, respectively, may be more precisely aligned with less splay between the jaw members 110 and 120, thereby facilitating knife blade 190 translation. Moreover, the strength of the flanges 113 and 123 is enhanced as well as the union therebetween, e.g., flat-on-flat abutting flange surfaces have more surface contact making the union therebetween stronger. The knife guide 133 may also be configured to pre-load jaw members 110 and 120 to help ensure proper alignment of knife channel halves 115a and 115b upon closing of the jaw members 110 and 120 as explained in more detail below.

As best shown in FIG. 6, blade guide 133 may include a blade stop or hook 135 disposed at a distal end thereof. The blade stop 135 may be integrally associated with the knife guide 133 (FIG. 6), the purpose of which is explained immediately below, or pivotably engaged with the knife guide 133, the purpose of which is explained with reference to FIG. 9. The relationship between flanges 113 and 123 and blade guide 133 is established by pivot pin 185 disposed through apertures 186a, 186b, and 186c, respectively, and by drive pin 180 disposed through slots 181a, 181b and 181c, respectively. Accordingly, when jaw members 110, 120 are in a first, or open, position, knife guide 133 pivots such the blade stop 135 interferes with the knife path 138, thereby preventing distal translation of knife blade 190. In one embodiment, this may be accomplished by the knife guide 133 including an elongated slot 181c that is cammed when the drive pin 180 is biased in a distal-most position such that the knife guide 133 and blade stop 135 pivot thereby obstructing the knife path 138. Alternatively, the blade stop 135 may pivot relative to the knife guide 133 to obstruct the knife path 138 (See FIG. 9). In this instance, the elongated slot 181c may be constructed as a pass-through or non-engaging slot.

When handles 30a and 30b are squeezed toward the housing 20, drive sleeve 17 and drive pin 180 are pulled proximally to close the jaw members 110 and 120, which also pivots the knife guide 133 so that the blade stop 135 no longer obstructs or interferes with the knife path 138. Thus, in this embodiment, the knife guide 133, by virtue of the blade stop 135, prevents distal advancement of knife blade 190 when jaw members 110 and 120 are in the first, open position and permits distal advancement of knife blade 190 when jaw members 110 and 120 are in the second, closed position.

Alternatively, a hook (not shown) may be disposed on either of flanges 113 or 123. The hook would operate in substantially the same manner as the blade stop 135 disposed on the blade guide 133 in the embodiment discussed above. Accordingly, as jaw members 110, 120 are opened, the hook on flange 113 or 123 is pivoted into the path of knife blade 190, thereby preventing distal translation of knife blade 190. When handles 30a and 30b are squeezed toward the housing 20, drive sleeve 17 and drive pin 180 are pulled proximally to close the jaw members 110 and 120. The pulling of drive pin 180 also pivots flanges 113 and 123, thereby closing the jaw members 110 and 120 and as a result, the hook is pivoted out of the path of knife blade 190.

Figure 4A:
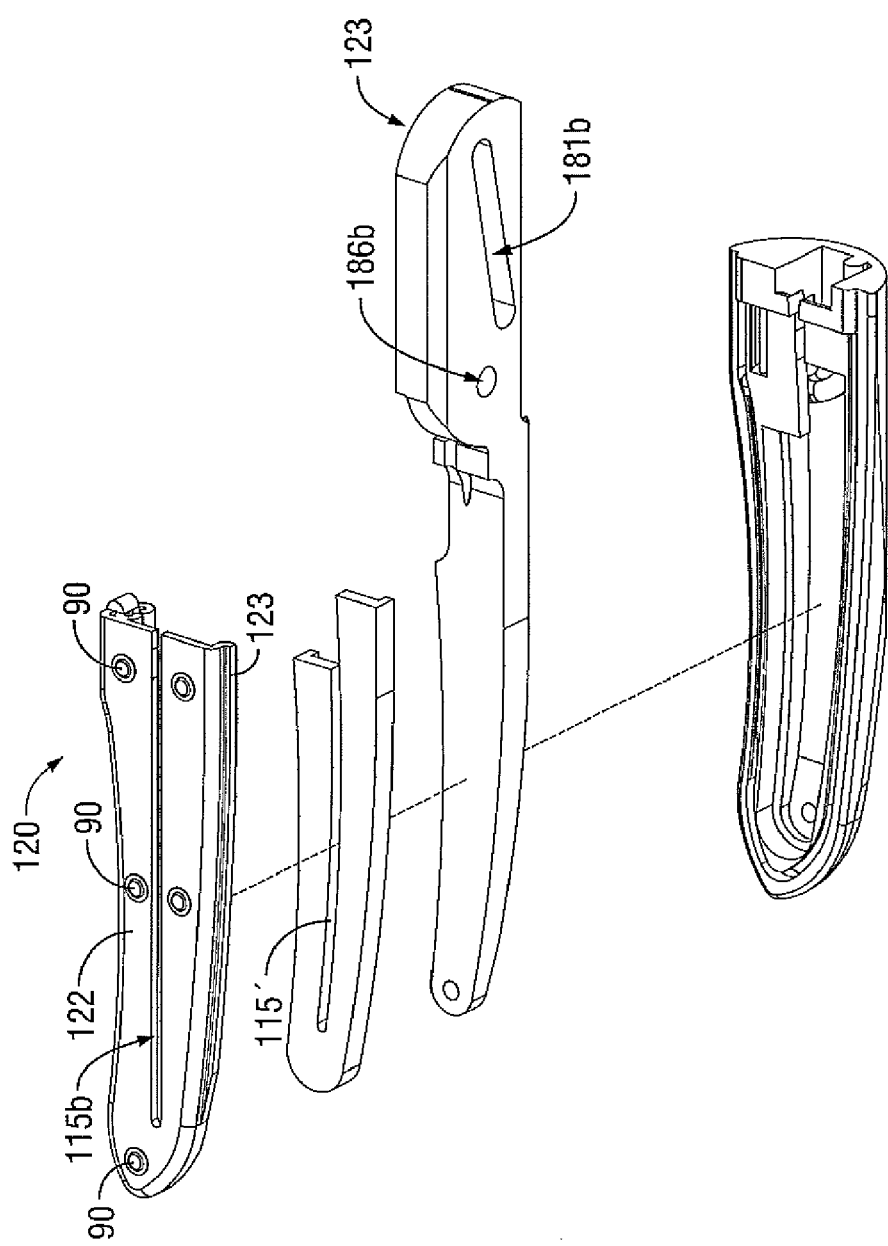
FIG. 4A is a greatly-enlarged, perspective view of the bottom jaw of the end effector assembly with parts separated.
Figure 4B:
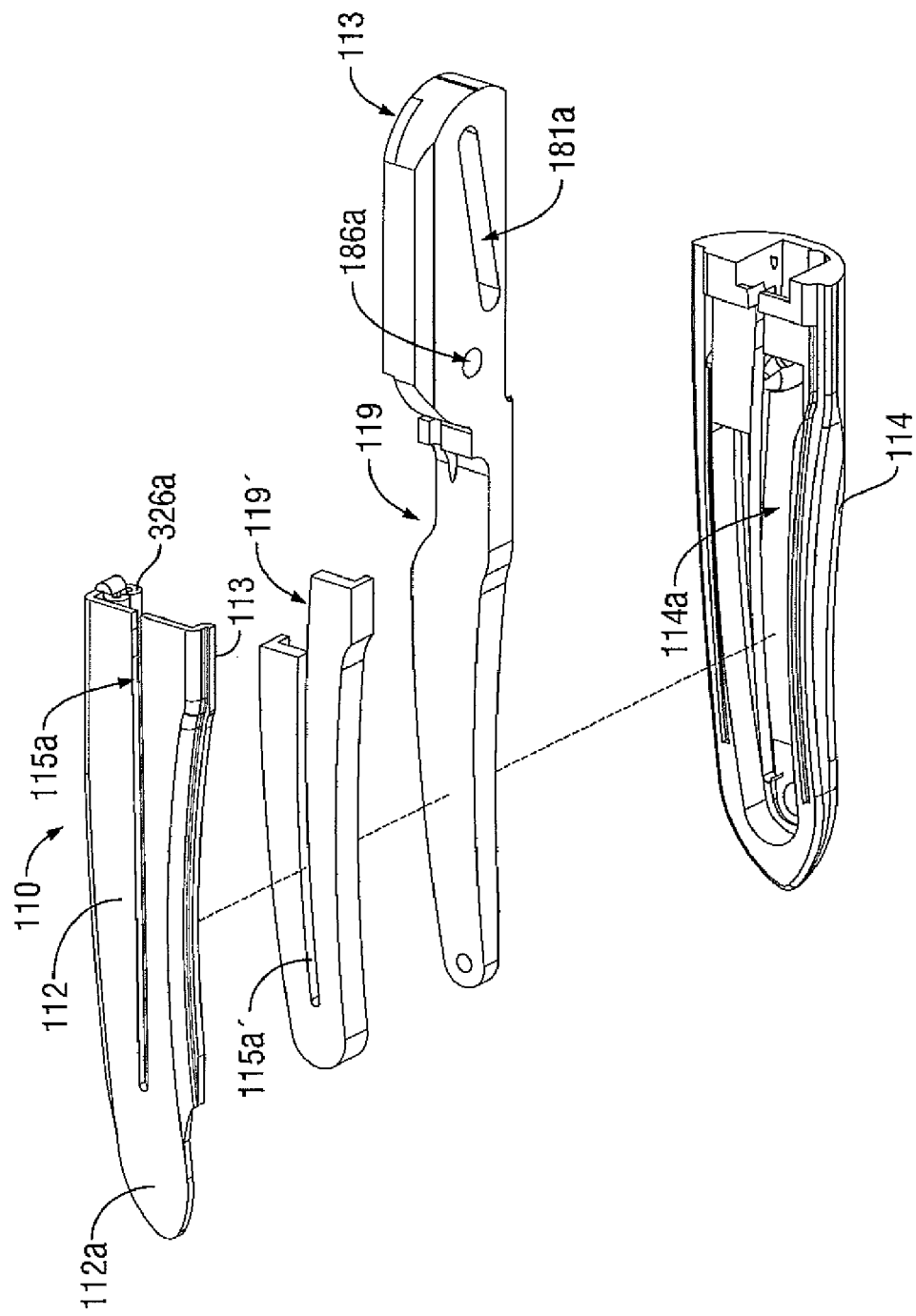
FIG. 4B is a greatly-enlarged, perspective view of the top jaw of the end effector assembly with parts separated.
Figure 5:
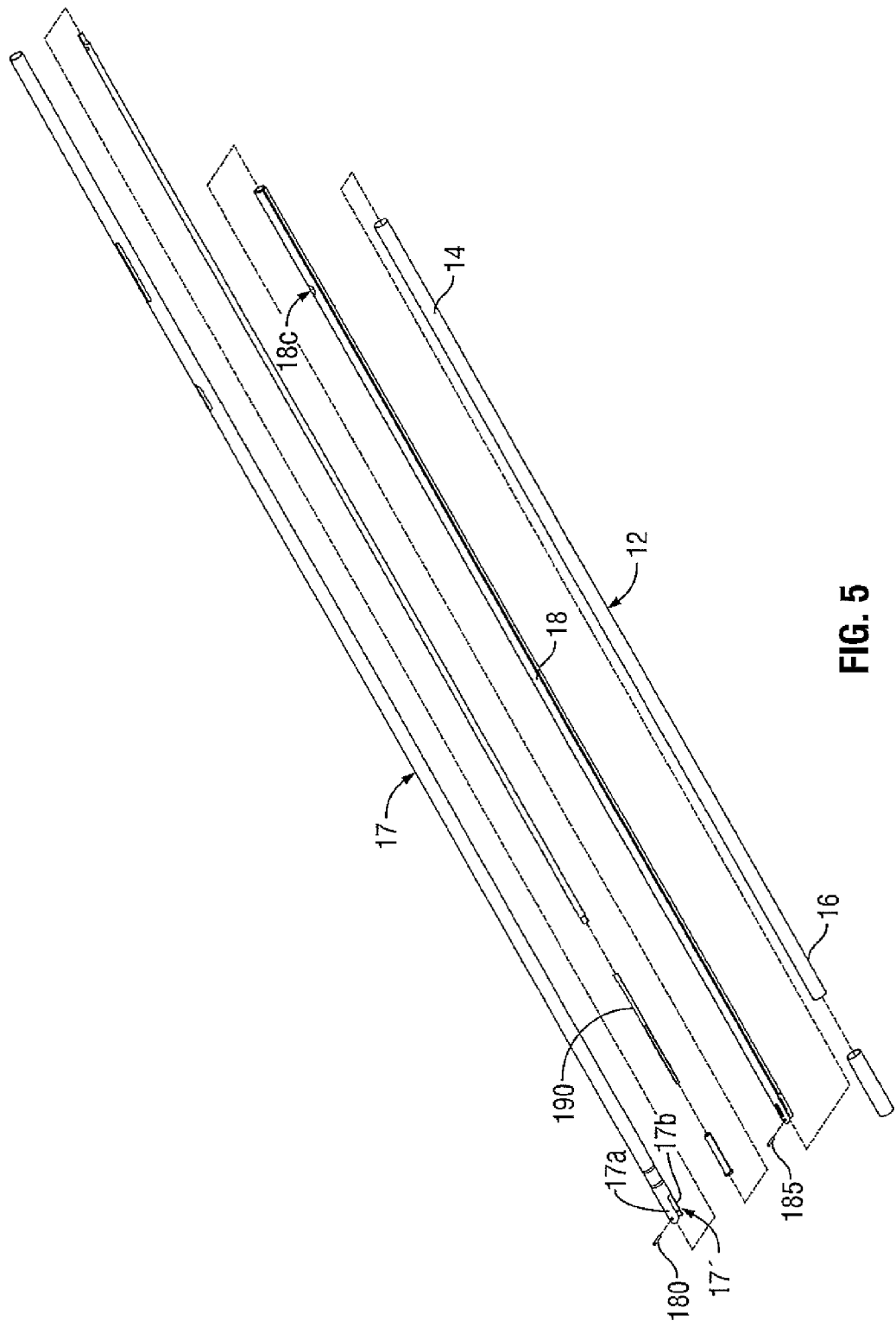
FIG. 5 is a greatly-enlarged, perspective view of the elongated shaft for housing various moving parts of the drive assembly and knife assembly.

As best shown in FIG. 4B, jaw member 110 also includes a support base 119 that extends distally from flange 113 and that is configured to support an insulative plate 119' thereon. Insulative plate 119', in turn, is configured to support an electrically conductive tissue engaging surface or sealing plate 112 thereon. Sealing plate 112 may be affixed atop the insulative plate 119' and support base 119 in any suitable manner, e.g., snap-fit, over-molding, stamping, ultrasonically welded, etc. Support base 119 together with the insulative plate 119' and electrically conductive tissue engaging surface 112 are encapsulated by an outer insulative housing 114. Outer housing 114 includes a cavity 114a that is dimensioned to securely engage the electrically conductive sealing surface 112 as well as the support base 119 and insulative plate 119'. This may be accomplished by stamping, by overmolding, by overmolding a stamped electrically conductive sealing plate and/or by overmolding a metal injection molded seal plate.

All of these manufacturing techniques produce jaw member 110 having an electrically conductive surface 112 that is substantially surrounded by an insulating substrate 114.

The electrically conductive surface or sealing plate 112 and the outer housing 114, when assembled, form longitudinally-oriented knife channel 115a defined therethrough for reciprocation of the knife blade 190. It is envisioned that the knife channel 115a cooperates with corresponding knife channel 115b defined in jaw member 120 to facilitate longitudinal extension of the knife blade 190 along a preferred cutting plane to effectively and accurately separate the tissue along the formed tissue seal. As discussed above, when knife blade 190 is deployed, at least a portion of knife blade 190 advances through knife path 138 and into knife channels 115a and 115b. In addition to the blade stop 135, handle 30a may includes a lockout flange (not shown) which prevents actuation of the knife assembly 70 when the handle 30a is open thus preventing accidental or premature activation of the knife blade 190 through the tissue. A more detailed discussion of the lockout flange is discussed in above-mentioned U.S. patent application Ser. No. 11/540,335.

As explained above and as illustrated in FIGS. 4A and 4B, in one embodiment, the knife channel 115 is formed when the jaw members 110 and 120 are closed. In other words, the knife channel 115 includes two knife channel halves—knife channel half 115a disposed in sealing plate 112 of jaw member 110 and knife channel half 115b disposed sealing plate 122 of jaw member 120. It is envisioned that the knife channel 115 may be configured as a straight slot with no degree of curvature which, in turn, causes the blade 190 to move through the tissue in a substantially straight fashion. Alternatively, and as shown, the knife channel 115 may be curved, which has certain surgical advantages. In the particular embodiment shown in FIGS. 6 and 7, the knife channel 115 (knife channel 115a shown) is curved and is offset from the centerline or longitudinal axis "A" of the forceps 10 by a distance "X" (See FIGS. 7 and 8). This offset distance "X" may be in the range of about 0.010 inches to about 0.040 inches.

The offset orientation of the knife blade 190 (by virtue or the knife guide 133 being assembled on one side of the flanges 113 and 123 allows the knife blade to enter the knife channel 115 in a substantially straight orientation thereby facilitating separation of tissue. Moreover, the knife blade 190 travels in a substantially straight manner through most of the knife channel 115 and is only forced to bend around the knife channel 115 towards a distal end of the jaw members 110 and 120. Further, the offset orientation of the knife channel, e.g., knife channel 115b, and the disposition of the knife blade 190 traveling through the knife guide 133 also enhances the cutting effect and reduces the chances of the knife blade 190 binding during translation (extension or retraction).

As mentioned above, when the jaw members 110 and 120 are closed about tissue, knife channels 115a and 115b form a complete knife channel 115 to allow longitudinal extension of the knife blade 190, from the knife path 138, in a distal fashion to sever tissue along a tissue seal. Knife channel 115 may be completely disposed in one of the two jaw members, e.g., jaw member 120, depending upon a particular purpose. It is also envisioned that jaw member 120 may be assembled in a similar manner as described above with respect to jaw member 110.

Figure 8:
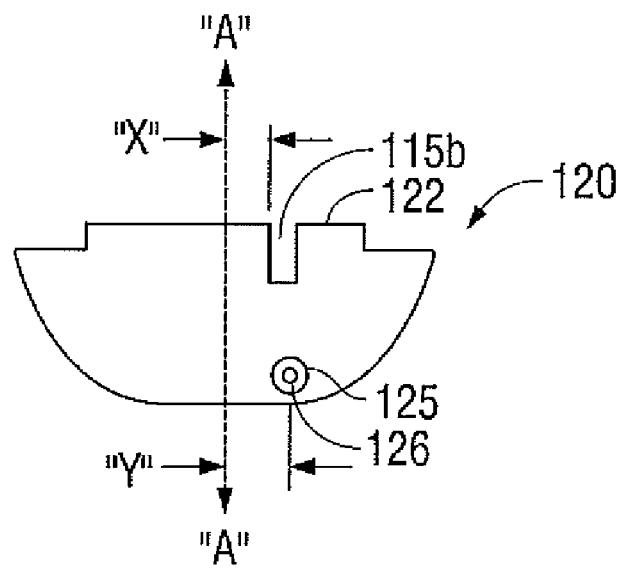
FIG. 8 is a rear, perspective view of one of the jaw members in accordance with an alternate embodiment of the present disclosure.

Referring now to FIGS. 6 and 8, electrical lead or wire 126 is shown extending from shaft 12 through knife housing 133 and entering wire tube 125 of jaw members 120. Wires 116 and 126 are used to supply electrical energy to electrically conductive sealing surfaces 112 and 122 of jaw members 110 and 120, respectively. In the embodiment of FIG. 6, knife housing 133 also acts as a wire guide, configured to guide wires 116 and 126 to jaw members 110 and 120. Electrical leads or wires 116 and 126 are protected by knife housing 133. Wire tube 125 (FIG. 8) of jaw member 120, may be offset from a longitudinal axis "Y" of the forceps 10 in the same direction as the offset knife channel 115b, such that knife channel 115b is disposed above the wire tube 125. The offset "X" of the knife channel, e.g., knife channel 115b, and the offset "Y" of the disposition of the electrical lead or wire 126 relative to longitudinal axis "A" may be different or the same depending upon a particular purpose or to facilitate manufacturing.

For example, in one embodiment, the offset distance "X" may be in the range of about 0.010 inches to about 0.040 inches whereas the offset distance "Yes" may be in the range about 0.040 inches to about 0.140 inches. In addition, particular "X" and "Y" configurations may be as follows: when "X" is about 0.010 inches "Y" may be about 0.040 inches; when "X" is about 0.017 inches "Y" may be about 0.070 inches; and when "X" is about 0.034 inches "Y" may be about 0.140 inches. Other configurations and offsets for "X" and "Y" are also contemplated and within the scope of this disclosure.

Figure 9:
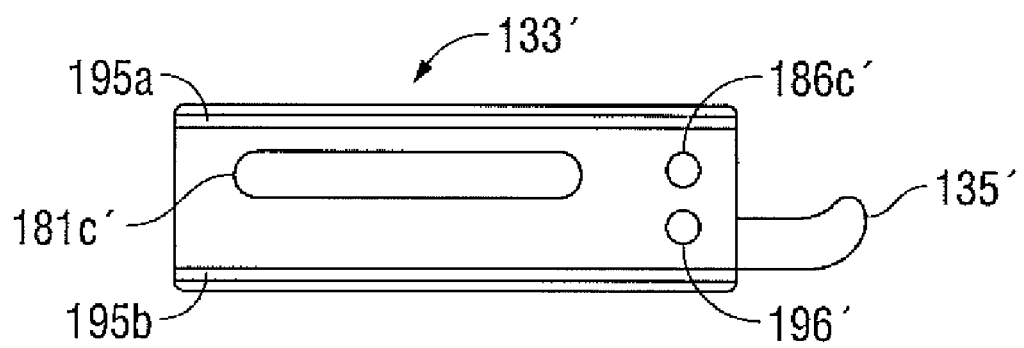
FIG. 9 is an enlarged side view of another embodiment of the knife guide according to the present disclosure.

FIG. 9 shows another embodiment of the knife guide 133' that includes similar features to the knife guide 133 described above such as elongated slot 181c', pivot hole 186c' and blade stop 135'. In this particular embodiment, the blade stop is moveable from a first position that interferes with the knife path 138 (See FIG. 7) to prevent distal translation of the knife 190 when the jaw members 110 and 120 are disposed in an first, open configuration to a second position that allows distal translation of the knife 190 when the jaw members 110 and 120 are disposed in the second, closed configuration. The blade stop 135' is pivotably engaged to the knife guide 133' and biased to obstruct with the knife path 138 when the jaw members 110 and 120 are disposed in the first, open configuration. Thus in this embodiment, the blade stop 135 prevents distal advancement of knife blade 190 when jaw members 110 and 120 are in the first, open configuration and permits distal advancement of knife blade 190 when jaw members 110 and 120 are in the second, closed configuration.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
a housing having a shaft attached thereto, the shaft having a longitudinal axis defined therethrough and an end effector assembly disposed at a distal end thereof, wherein the end effector assembly includes:
first and second jaw members disposed in opposing relation relative to one another and moveable from a first position to a second position for grasping tissue therebetween, each of the jaw members including a proximal flange adapted to communicate with a drive assembly for moving the jaw members between the first and second positions and at least one of the jaw members including a knife channel defined therein, a proximal end of the knife channel offset from the longitudinal axis defined through the shaft, at least one of the jaw members adapted to connect to an electrosurgical energy source to communicate energy to tissue disposed between the jaw members; and
a knife guide assembled adjacent an outer surface of one of the proximal flanges of the jaw members on the same side as the proximal end of the knife channel, the knife guide defining a knife path therein that is configured to guide a knife into the knife channel for translation therethrough, wherein the knife guide includes a channel defined therein for guiding an electrical lead to the at least one of the jaw members for supplying electrosurgical energy thereto.

2. A forceps according to claim 1, wherein the forceps includes at least one handle that operably couples to a drive assembly for moving the jaw members between the first and second positions.

3. A forceps according to claim 2, wherein the proximal flanges of the end effector and the knife guide include elongated slots defined therethrough that cooperate with a drive pin operably connected to the drive assembly to move the jaw members from the first position to the second position.

4. A forceps according to claim 3, wherein the elongated slots of the proximal flanges are cam slots that operably engage the drive pin and the elongated slot of the knife guide is a pass-through slot.

5. A forceps according to claim 1, wherein a distal portion of the knife channel is curved.

6. A forceps according to claim 5, wherein the offset knife channel and the disposition of the knife guide relative to the longitudinal axis facilitate substantially straight extension of the knife through the knife channel along a substantial length of the knife channel.

7. A forceps according to claim 1, wherein the proximal end of the knife channel is offset a distance X relative to the longitudinal axis defined through the forceps, wherein X is in the range of about 0.010 inches to about 0.040 inches.

8. A forceps according to claim 1, wherein the knife channel is defined within both the first and second jaw members and the knife guide is configured to preload the jaw members during assembly for ensuring proper alignment of the knife channels.

9. A forceps, comprising:
a housing having a shaft attached thereto, the shaft having a longitudinal axis defined therethrough and an end effector assembly disposed at a distal end thereof, wherein the end effector assembly includes:
first and second jaw members disposed in opposing relation relative to one another and moveable from a first configuration to a second configuration for grasping tissue therebetween, each of the jaw members including a proximal flange adapted to communicate with a drive assembly for moving the jaw members between the first and second configuration and at least one of the jaw members including a knife channel defined therein, a proximal end of the knife channel offset from the longitudinal axis defined through the shaft; and
a knife guide assembled adjacent an outer surface of one of the proximal flanges of the jaw members on the same side as the proximal end of the knife channel, the knife guide defining a knife path therein that is configured to guide a knife into the knife channel for translation therethrough, the knife guide including a blade stop at a distal end thereof, the blade stop positionable from a first position that interferes with the knife path to prevent distal translation of the knife when the jaw members are disposed in the first configuration to a second position that allows distal translation of the knife when the jaw members are disposed in the second configuration.

10. A forceps according to claim 9, wherein the blade stop is pivotably engaged to the knife guide and biased to obstruct the knife path when the jaw members are disposed in the first, open configuration.

11. A forceps according to claim 9, wherein the forceps includes at least one handle that operably couples to a drive assembly for moving the jaw members between the first and second configurations.

12. A forceps according to claim 11, wherein proximal flanges of the end effector and the knife guide include elongated slots defined therethrough that cooperate with a drive pin operably connected to the drive assembly to move the jaw members from the first configuration to the second configuration.

13. A forceps according to claim 12, wherein the elongated slots of the proximal flanges are cam slots that operably engage the drive pin and the elongated slot of the knife guide is a pass-through slot.

14. A forceps according to claim 9, wherein at least one of the jaw members is adapted to connect to an electrosurgical energy source to communicate energy to tissue disposed between the jaw members.

15. A forceps according to claim 14, wherein the knife guide includes a channel defined therein for guiding an electrical lead to at least one of the jaw members for supplying electrosurgical energy thereto.

16. A forceps according to claim 9, wherein a distal portion of the knife channel is curved.

17. A forceps according to claim 16, wherein the offset knife channel and the disposition of the knife guide relative to the longitudinal axis facilitate substantially straight extension of the knife through the knife channel along a substantial length of the knife channel.

18. A forceps according to claim 9, wherein the proximal end of the knife channel is offset a distance X relative to the longitudinal axis defined through the forceps, wherein X is in the range of about 0.010 inches to about 0.040 inches.

* * * * *